US010025909B2

(12) United States Patent
Gray et al.

(10) Patent No.: US 10,025,909 B2
(45) Date of Patent: Jul. 17, 2018

(54) MEDICAL DEVICES AND CONFIGURATION UPDATE MANAGEMENT

(71) Applicant: Ivenix, Inc., Amesbury, MA (US)

(72) Inventors: George W. Gray, North Andover, MA (US); William C. McQuaid, Melrose, MA (US)

(73) Assignee: Ivenix, Inc., Amesbury, MA (US)

( * ) Notice: Subject to any disclaimer, the term of this patent is extended or adjusted under 35 U.S.C. 154(b) by 0 days.

(21) Appl. No.: 14/794,231

(22) Filed: Jul. 8, 2015

(65) Prior Publication Data

US 2016/0034655 A1     Feb. 4, 2016

Related U.S. Application Data

(60) Provisional application No. 62/032,872, filed on Aug. 4, 2014.

(51) Int. Cl.
    *G16H 40/40*      (2018.01)
    *A61M 5/142*      (2006.01)
    *G06F 19/00*      (2018.01)

(52) U.S. Cl.
    CPC ......... *G06F 19/3468* (2013.01); *A61M 5/142* (2013.01); *G16H 40/40* (2018.01);
(Continued)

(58) Field of Classification Search
    CPC ............ G06F 19/3412; G06F 19/3468; A61M 5/142; A61M 2205/3553; A61M 2205/3561
See application file for complete search history.

(56) References Cited

U.S. PATENT DOCUMENTS 5,681,285 A    10/1997   Ford et al.
5,772,635 A *   6/1998   Dastur ................. A61M 5/172
                                          604/131
(Continued)

FOREIGN PATENT DOCUMENTS

JP          2007-026254 A    2/2007
KR    10-2012-0133628 A1   12/2012
KR       10-1247867 B1     3/2013

OTHER PUBLICATIONS

Search Report, PCT/US2015/042613, dated Nov. 17, 2015, pp. 4.

*Primary Examiner* — Terrell Johnson
(74) *Attorney, Agent, or Firm* — Chapin IP Law, LLC

(57) ABSTRACT

A configuration management resource keeps track of incremental updates to a locally stored copy of configuration information (such as drug library information) used by a medical device to administer treatment to patients. The medical device retrieves a copy of the configuration information from a configuration management resource. Unbeknownst to a user of the medical device, to ensure that the medical device has most up-to-date configuration information, the medical device communicates a request for updates to the configuration management resource. To service the received request for updated configuration information, the configuration management resource forwards incrementally available configuration update information to the requesting medical device. The medical device uses the received configuration update information from the configuration management resource to update its local version of configuration information stored in the medical device.

42 Claims, 10 Drawing Sheets

(52) U.S. Cl.
CPC ............... *A61M 2205/3553* (2013.01); *A61M 2205/3561* (2013.01)

(56) References Cited

U.S. PATENT DOCUMENTS

| | | | |
|---|---|---|---|
| 2006/0100746 A1* | 5/2006 | Leibner-Druska | A61M 5/14 700/282 |
| 2007/0214003 A1 | 9/2007 | Holland et al. | |
| 2009/0125336 A1* | 5/2009 | Wehba | G06F 19/3456 705/3 |
| 2010/0198196 A1 | 8/2010 | Wei | |
| 2011/0264044 A1* | 10/2011 | Bartz | A61M 5/14212 604/151 |
| 2012/0066609 A1 | 3/2012 | Howard et al. | |
| 2012/0197196 A1* | 8/2012 | Halbert | A61M 5/142 604/151 |
| 2013/0036414 A1* | 2/2013 | Birtwhistle | G06F 8/65 717/173 |
| 2013/0104120 A1* | 4/2013 | Arrizza | G06F 8/65 717/173 |
| 2013/0162160 A1* | 6/2013 | Ganton | H05B 37/02 315/210 |
| 2016/0034655 A1* | 2/2016 | Gray | G06F 19/3468 713/1 |

\* cited by examiner ments of the invention.

MEDICAL DEVICES AND CONFIGURATION UPDATE MANAGEMENT

RELATED APPLICATIONS

This application claims the benefit of U.S. Provisional Patent Application Ser. No. 62/032,872 entitled "Transparent Configuration Management," filed on Aug. 4, 2014, the entire teachings of which are incorporated herein by this reference.

BACKGROUND

Medical devices such as intravenous fluid delivery pumps have become more sophisticated over the years. For example, conventional fluid delivery pumps are sometimes equipped with wireless capability enabling them to communicate over a respective network to a server resource. Via communications over a respective wireless communication link with the server resource, the fluid delivery pump is able to perform any of multiple functions.

One type of function performed by a fluid delivery pump is to retrieve a so-called drug library. The drug library includes configuration information about many different types of drugs that can be dispensed from the fluid delivery pump.

During operation, the fluid delivery pump uses the drug library to obtain configuration information about one or more drugs to be delivered to a respective patient. Subsequent to retrieval, the fluid delivery pump uses the obtained configuration information to facilitate delivery of the one or more drugs to a respective patient.

BRIEF DESCRIPTION OF EMBODIMENTS

Embodiments herein include novel approaches to distributing and/or updating configuration information associated with medical devices.

More specifically, in one embodiment, a configuration management resource manages updating and distribution of configuration information stored in a repository. The stored configuration information can include multiple sets of configuration information; each of the sets of configuration information can be updated at different times depending upon publication of updates by a respective administrator or other resource. As the configuration management resource receives an update to a particular set of configuration information stored in the repository, the configuration management resource applies the received update to the particular set of configuration information. Subsequent to updating, the configuration management resource manages incremental distribution of the updated configuration information stored in the repository to one or more medical devices as described herein.

As an illustrative example, assume that a medical device operating in a healthcare enterprise communicates a request for configuration update information over a communication link to the configuration management resource. As previously discussed, the configuration management resource applies and keeps track of updates to configuration information (such as drug library information) stored in a repository. To service the request for updated configuration information, the configuration management resource forwards configuration update information to the requesting medical device. The medical device uses the received configuration update information to update a current version of configuration information stored in the medical device. In one embodiment, the current version of configuration information present in the medical device facilitates providing healthcare service to a patient. In one embodiment, the configuration update information received by the medical device represents incremental changes to updated configuration information.

Accordingly, via the configuration update information, the medical device is kept up-to-date as changes are released for distribution by the configuration management resource or other entity.

In accordance with further embodiments, the wireless medical device can be a medical infusion pump for delivering fluids to a respective recipient such as a patient in a healthcare environment. The configuration update information pertains to a specific set of configuration information (such as for a particular drug) stored in the medical device. In response to receiving the configuration update information, to update the specific set of configuration information, a configuration management resource (device manager) in the medical device applies the incremental configuration update information to the specific set of configuration information stored in the medical device.

In accordance with yet further embodiments, when updating the specific set of configuration information using the configuration update information, the configuration management resource in the medical device stores the configuration publish time information (such as version number or letter, date, clock value, etc.) indicating when the specific set of configuration information was last updated. Use of the time information makes it possible to identify the latest versions of configuration information as further discussed herein.

These and other more specific embodiments are disclosed in more detail below.

Note that any of the resources as discussed herein can include one or more computerized devices, medical devices, infusion pumps, fluid delivery systems, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (i.e., any physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware or shortcode in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes a computer readable storage medium and/or system having instructions stored thereon. The instructions, when executed by computer processor hardware, cause the computer processor hardware to: communicate a request for configuration update information over a communication link to a configuration management resource; receive the configuration update information over the communication link from the configuration management resource; and utilize the received configuration update information to update a current version of configuration information stored in the medical device, the current version of configuration information present in the medical device to provide healthcare service to a patient.

Another embodiment herein includes a computer readable storage medium and/or system having instructions stored thereon. The instructions, when executed by computer processor hardware, cause the computer processor hardware to: receive an update to a particular set of configuration information stored in a repository; apply the received update to the particular set of configuration information; and manage distribution of the configuration information stored in the repository, the configuration information including multiple sets of configuration information including the particular set of configuration information for distribution to medical devices.

The ordering of the operations above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for managing and facilitating distribution of configuration updates to one or more medical devices. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty. For additional details and/or possible perspectives (permutations) of the invention(s), the reader is directed to the Detailed Description section and corresponding figures of the present disclosure as further discussed below.

Figure 1:
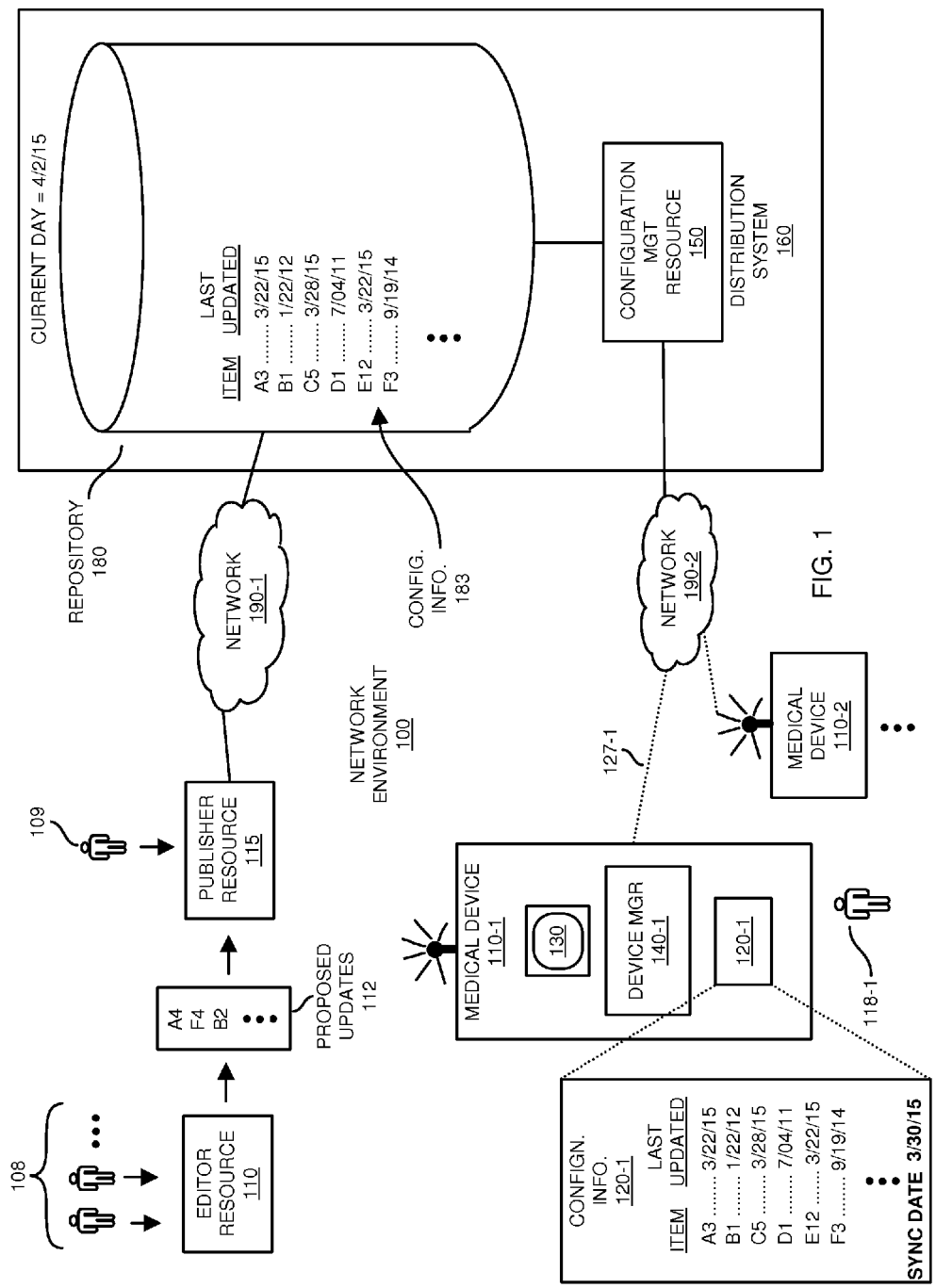
FIG. 1 is an example diagram illustrating implementation of a configuration management system and corresponding components according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

Now, more specifically, FIG. 1 is an example diagram illustrating a configuration management system according to embodiments herein.

As shown in this example embodiment, network environment 100 includes one or more users 108 (such as doctors, healthcare professionals, pharmacists, etc.), editor resource 111, proposed updates 112, administrator 109, publisher resource 115, network 190-1, configuration management system 160, network 190-2, and multiple medical devices 110 (such as including medical device 110-1, medical device 110-2, etc.).

Note that the medical devices 110 as described herein can be any suitable type of device. For example, in one embodiment, each of the medical devices 110 is an intravenous infusion pump use for delivery of fluid to a respective recipient. Each infusion pump can be configured to support different types of functionality such as first functionality supporting retrieval of configuration information 183 (such as drug library information) over a network connection from a remote server resource disparately located with respect to the medical infusion pump, second functionality supporting pumping of fluid from the medical infusion pump to a recipient based upon the retrieved configuration information, and so on.

As shown, the configuration management resource 150 manages storage of configuration information 183 in a repository 180. In this example embodiment, the stored configuration information 183 includes multiple sets of configuration information associated with multiple different types of items (such as drug delivery configuration information) A, B, C, D, E, etc.

In this example embodiment, the repository 180 stores: configuration information A3 (such as a third version of configuration information A), configuration information B1 (such as a first version of configuration information B), configuration information C5 (such as a fifth version of configuration information C), configuration information D1 (such as a first version of configuration information D), configuration information E12 (such as a $12^{th}$ version of configuration information E), configuration information F3 (such as a third version of configuration information F), etc.

By way of non-limiting example embodiment, and as previously discussed, the configuration information 183 stored in the repository 180 can represent any suitable type of information such as a drug library of configuration information. In such an instance, each of the items such as A, B, C, D, etc., represents a different drug in the drug library. The respective configuration information (such as configuration information A3, configuration information B1, etc.) for each respective drug can indicate any suitable type of information such as volume flow control parameters for delivering the respective drug to a target recipient, drug interference with other drugs, pump settings, etc.

In one embodiment, each of the sets of configuration information represents independently maintained information specifying how to administer a corresponding treatment (such as a particular drug) to the patient using the medical device. In addition to delivery control information used by the respective medical device to deliver the particular drug to a recipient, the independent information can specify drug interaction information associated with other drugs so that the caregiver operating the medical device 110-1 does not inadvertently harm the patient.

As each of the different sets of configuration information is updated in repository 180, the configuration management resource 150 keeps track of when a respective version of configuration information was last updated. As a specific example, the one or more users 108 execute editor resource 111 to modify and/or update configuration information associated with each of the items such as A3, B1, C5, D1, E12, F3, etc.

As will be further discussed below, note that each of the sets of configuration information can be updated at different times depending upon publication by a respective administrator or other resource. For example, as the configuration management resource 150 receives an update to a particular set of configuration information stored in the repository 180, the configuration management resource 150 applies the received update to the appropriate particular set of configuration information.

In this example embodiment, the one or more users 108 generates proposed updates 112 including: i) an update to configuration information A to new version A4, ii) an update to configuration information F to new version F4, iii) an update to configuration information B to new version B2, etc.

If desired, the proposed updates 112 are not made available for updating the configuration information 183 until the administrator 109 uses the publisher resource 115 to publish the proposed updates 112 for distribution over network 190-1 to the configuration management resource 150.

Further in this example, assume that prior to publishing the proposed updates 112 for distribution to configuration management resource 150, the respective user 118-1 operates the medical device 110-1. In one embodiment, the device manager 140-1 of medical device 110-1 communicates over network 190-2 to the configuration management resource 150 to obtain most up-to-date configuration information stored in repository 180 for storage in the medical device 110-1 as configuration information 120-1 (such as a copy of the configuration information 183).

In this example, the device manager 140-1 keeps track of the last day in which the corresponding portions of configuration information 120-1 were last published. If the medical device 110-1 is new and has no configuration information, the medical device 110-1 retrieves all of the configuration information 183 and stores it as a copy (configuration information 120-1) in the medical device 110-1.

As will be further discussed in the specification, when updates to configuration information 183 are available, the process of synchronizing the configuration information 120-1 with the configuration 183 can include communicating over a respective wireless communication link 127-1 through network 190-2 to configuration management resource 150. Via communications with the configuration management resource 150, the device manager 140-1 of the medical device 110-1 retrieves configuration updates and stores applies the updates to configuration information 120-1.

In addition to receiving updates, in one embodiment, the device manager 140-1 keeps track of configuration publish time information such as version number, clock value (such as year, day, hour, minute, second, etc.), etc., indicating when the corresponding configuration information for a drug was published by the administrator 109.

After synchronizing the configuration information 120-1 in the medical device 110-1 with respect to the configuration information 183 stored in repository 180 on Mar. 30, 2015, the configuration information 183 can be updated and distributed as discussed in the following FIGS.

In this example embodiment, the configuration information 120-1 indicates that: configuration information A3 was published on Mar. 22, 2015; configuration information B1 was published on Jan. 22, 2012; configuration information C5 was published on Mar. 28, 2015; configuration information D1 was published on Jul. 4, 2011; and so on.

Figure 2:
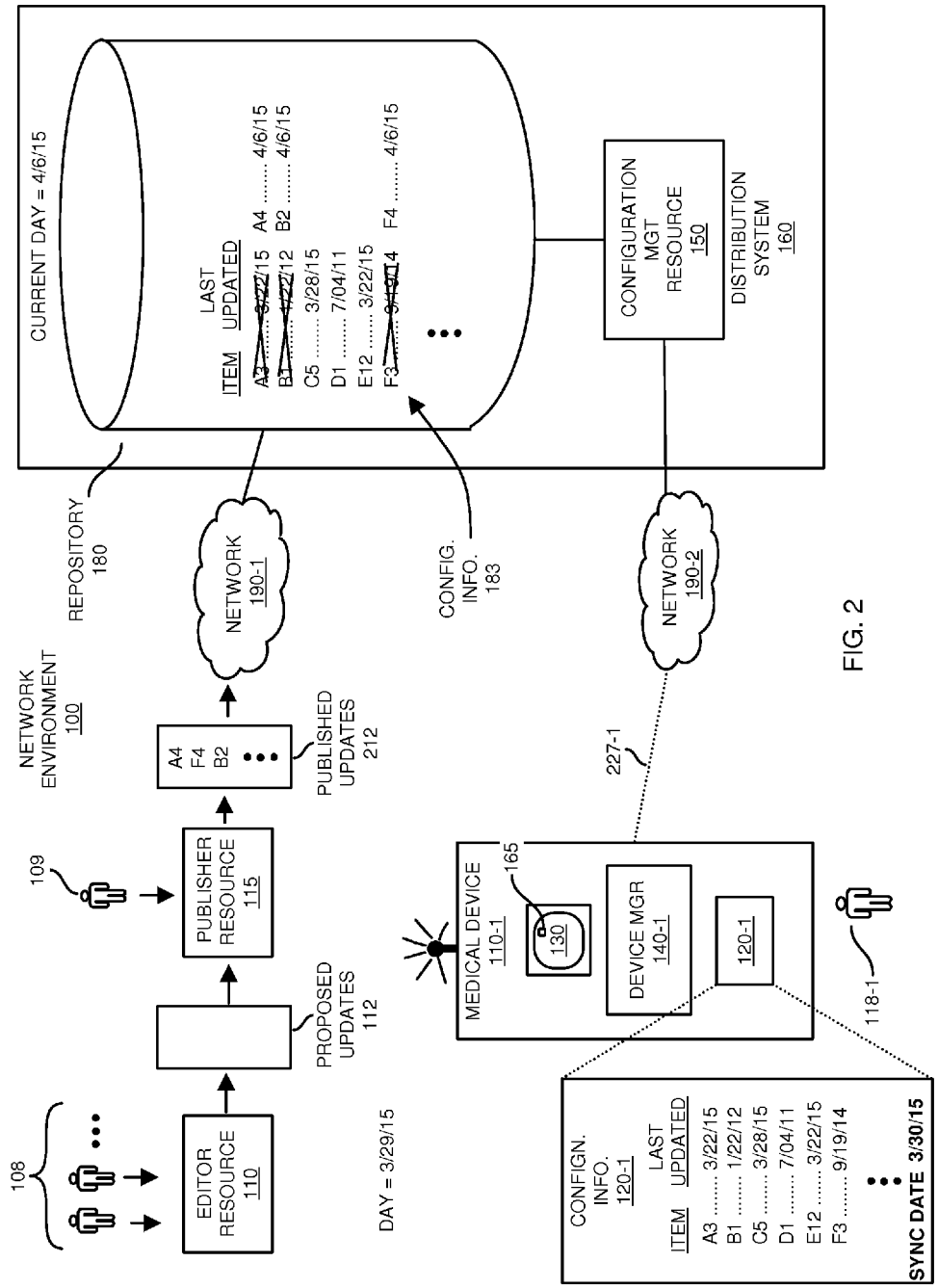
FIG. 2 is an example diagram illustrating an implementation of incrementally updating portions of configuration information according to embodiments herein.

FIG. 2 is an example diagram illustrating an implementation of incrementally updating portions of configuration information according to embodiments herein.

In this example as shown, the administrator 109 utilizes the publisher resource 115 to publish the proposed updates 112. In response to publishing the proposed updates 112 as published updates 212, the configuration manager resource 150 updates the configuration information 183 stored in repository 180.

More specifically, on Apr. 6, 2015, such as the day that the administrator 109 publishes the proposed updates 112 as published updates 212, the configuration manager resource 150 receives the published updates 212 over network 190-1 and applies them to the configuration information 183 stored in repository 180.

Application of the published updates 212 to the configuration information 183 can include replacing one or more specified portions of the current version of configuration information 183 in repository 180 with the appropriate published updates 212 (configuration update information). Alternatively, application of the published updates 212 can include modifying one or more specified portions of the current version of configuration information 183 in a manner as specified by the published updates 212 (configuration update information).

As a more specific example as shown in FIG. 2, based on availability of published updates 212, the configuration management resource 150 receives an update to configuration information A3 stored in repository 180. In accordance with the published updates 212, the configuration management resource 150 updates the configuration information A3 to configuration information A4. In one embodiment, this includes incrementally updating the appropriate portion of the configuration information 183 (such as configuration information A3). Additionally, the configuration management resource 150 keeps track of the date and time that the configuration information A is published using an appropriate method such as using timestamp information 4/6/15. Because the configuration information A3 in this example is updated to configuration information A4 on Apr. 6, 2015, the configuration manager resource 150 stamps the configuration A4 with the time information update of Apr. 6, 2015. As previously discussed, the time information update can include the time of day that the respective configuration information A4 was published.

Further in this example, based on published updates 212, the configuration management resource 150 receives an update to configuration information F3 stored in repository 180. In accordance with the published updates 212, the configuration management resource 150 updates the configuration information F3 in repository 180 to configuration information F4. In one embodiment, in a manner as previously discussed, in addition to incrementally updating the appropriate portion of the configuration information 183 (such as configuration information F3), the configuration management resource 150 keeps track of the date and/or time that the configuration information F is published using appropriate time stamp information. Because the updated configuration information F4 in this example is published on Apr. 6, 2015, the configuration manager resource 150 stamps the configuration F4 stored in repository 180 with the publication timestamp of Apr. 6, 2015.

Yet further in this example, based on published updates 212, the configuration management resource 150 receives an update to configuration information B1 stored in repository 180. In accordance with the published updates 212, the configuration management resource 150 updates the configuration information B1 to configuration information B2. In one embodiment, in addition to incrementally updating the appropriate portion of the configuration information 183 (such as configuration information B1), the configuration management resource 150 keeps track of the date and/or time that the configuration information B2 is published using appropriate time stamp information Apr. 6, 2015.

Accordingly, via published updates 212, the configuration manager resource 150 updates configuration information 183 stored in repository 180 so that each of the entries includes most up-to-date configuration information and corresponding publication information for a respective item. Subsequent to updating the configuration information 183, as further discussed below, the configuration management resource 150 makes the configuration information 183 and/or updated portions thereof available for distribution to medical devices 110 over network 190-2.

Figure 3:
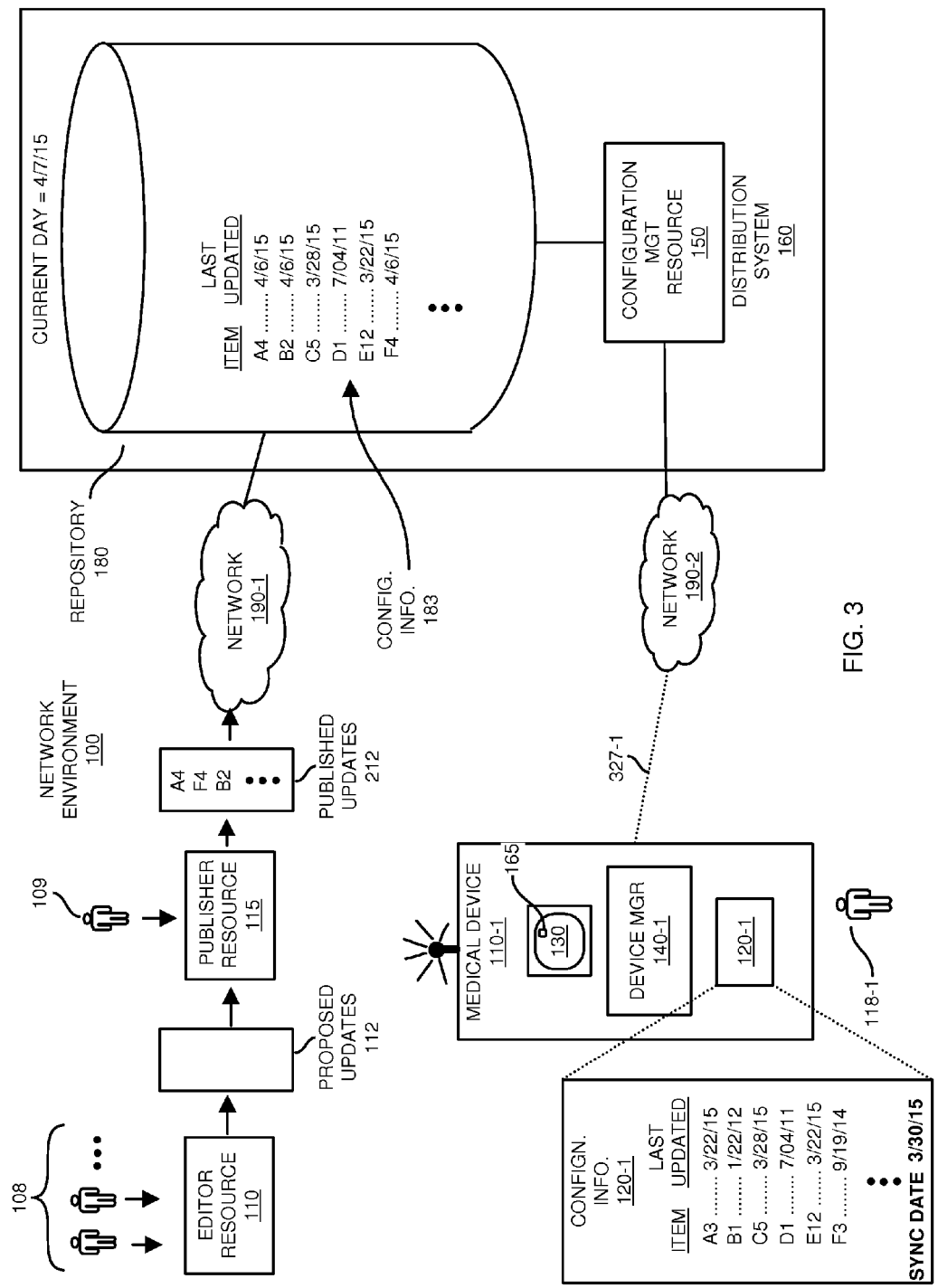
FIG. 3 is an example diagram illustrating availability of updated configuration information according to embodiments herein.

FIG. 3 is an example diagram illustrating updated configuration information according to embodiments herein.

Assume in this example embodiment, that user 118-1 (such as a caregiver) operates the medical device 110-1 on Apr. 7, 2015. Note that this is one day after the configuration information 183 in repository 180 is updated using the published updates 212 as previously discussed with respect to FIG. 2.

In accordance with one embodiment, upon activation of the medical device 110-1, the device manager 140-1 establishes the wireless communication link 327-1 with network 190-2 to check whether any updates are available for the configuration information 120-1 stored in the medical device 110-1. In one embodiment, the check for updates is automatically performed unbeknownst to the user 118-1. This alleviates the user 118-1 from having to keep track of whether the configuration information 120-1 stored in the medical device 110-1 is up-to-date before use.

Note that the device manager 140-1 can be configured to check for updates associated with the configuration information 183 in accordance with any suitable type of trigger event. For example, the device manager 140-1 can be configured to check for updates associated with the configuration information 183 unbeknownst to the respective user 118-1 at prescheduled times if desired. The check for updates can be scheduled at suitable times (such as every 5 minutes) or triggered by any suitable event (such as powering of the medical device 110-1 to administer a respective drug to a target recipient).

Alternatively, if desired, the user 118-1 can manually provide input to the medical device 110-1 to initiate update and synchronization of the configuration information 120-1 with the configuration information 103 stored in repository 180.

Figure 4:
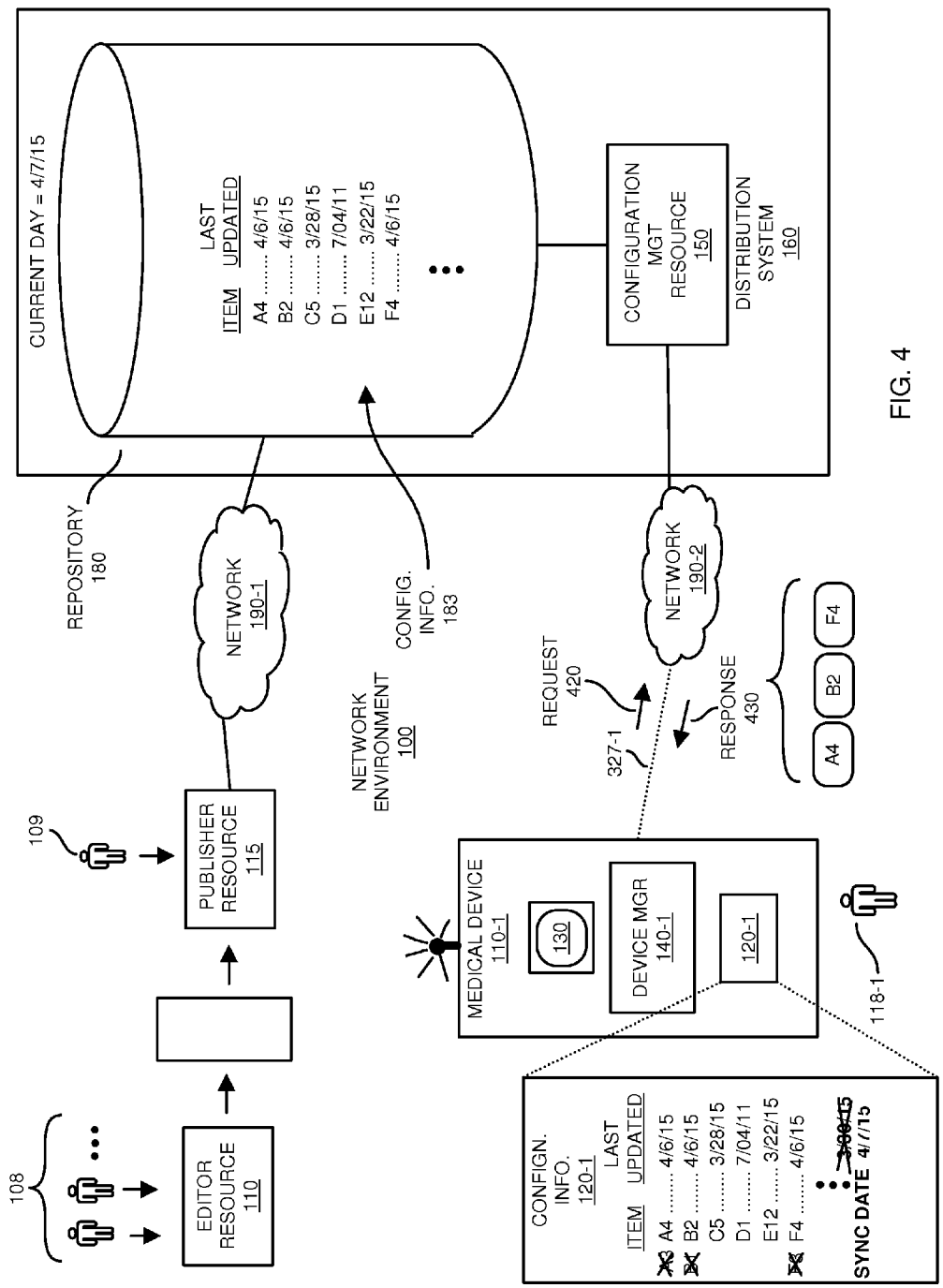
FIG. 4 is an example diagram illustrating distribution of updated configuration information according to embodiments herein.

FIG. 4 is an example diagram illustrating distribution of updated configuration information according to embodiments herein.

In response to a trigger event such as executing a preliminary setup operation to administer a drug to a patient, the medical device 110-1 can be configured to establish communication link 327-1 between medical device 110-1 and the configuration management resource 150. In one embodiment, the communication link 327-1 is a secured wireless communication link in communication with a resource such as a wireless access point disposed in network 190-2. The resource supports communications through network 190-2 to the configuration management resource 150.

Further in this example embodiment, the medical device 110-1 communicates a request 420 for available configuration update information over communication link 327-1 to the configuration management resource 150.

As previously discussed, the configuration manager resource 150 keeps track of updates applied to configuration information 183 (such as drug library information) stored in repository 180.

To service the received request 420, the configuration manager resource 150 determines which, if any, of the portions of configuration information 183 to forward to the medical device 110-1.

As further shown in this example embodiment, the configuration management resource 150 selects which configuration update information (e.g., a fewer than all portion of the configuration information 183) to distribute to the medical device 110-1 based on a comparison of a publish time of last configuration update resident on the medical device 110-1 and a time value indicating the publish time of the respective portions of configuration information 183 stored in repository 180. As further discussed below, based on the comparison, the configuration management resource 150 forwards incremental changes to configuration information 183 over the wireless communication link through 127-1 to the medical device 110-1 to update the configuration information 120-1.

As a more specific example, the device manager 140-1 of medical device 110-1 forwards the last publication time information for each set of configuration information over network 190-2 (potentially along with request 420 or subsequent communications) to the configuration manager resource 150. The configuration management resource 150 utilizes the received last publication information of configuration information 120-1 stored in medical device 110-1 to identify which, if any, portions of the configuration information 183 should be forwarded over network 190-2 to the device manager 140-1 of medical device 110-1 for incrementally updating appropriate portions of configuration information 120-1.

In the present example, based on a comparison of the received last publication information for each set of configuration information, the configuration management resource 150 determines that configuration information A4, configuration information B2, and configuration information F4 were published subsequent to corresponding publication dates associated with A3, B1, and F3 stored in configuration information 120-1. That is, the configuration information A4 was published Apr. 6, 2015; the configuration information B2 was published on Apr. 6, 2015; the configuration information F4 was published on Apr. 6, 2015; and so on.

In such an instance, based upon the comparison of time information as previously discussed, because it is known that the configuration information A4, B2, and F4 have not yet been forwarded to the medical device 110-1, the configuration management resource 150 forwards the updated configuration information A4, B2, F4, etc., in the response 430 to the device manager 140-1 of medical device 110-1.

Accordingly, the configuration management resource 150 can be configured to utilize the received publication information for each set of configuration information as a filter parameter to identify which of the incremental changes to the configuration information 183 to transmit to the device manager 140-1 for updating the configuration information 120-1.

As further shown in FIG. 4, the device manager 140-1 utilizes the received updated configuration information A4, B2, F4, etc., to update the appropriate portions of the configuration information 120-1.

In one embodiment, the device manager 140-1 maps each of the received configuration update information A4, B2, F4, etc., to the corresponding current versions of the configuration information A3, B1, F3, etc. The medical device 110-1 utilizes the received configuration update information A4, B2, F4, etc., to update the current version of configuration information A3, B1, F3, etc., stored in the medical device 110-1.

More specifically, the device manager 140-1 updates the configuration information A3 to newly received configuration information A4; the device manager 140-1 updates the configuration information B1 to the newly received configuration information B2; the device manager 140-1 updates the configuration information F3 to newly received configuration information F4; and so on.

In accordance with yet further embodiments, when updating the specific set of configuration information using the received configuration update information A4, B2, F4, etc., the device manager 140-1 in the medical device 110-1 stores time information indicating when the (such as version number or letter, date, clock value, etc.) specific set of configuration information was published. For example, for the updated configuration information A4, the device manager 140-1 indicates the publication date of Apr. 6, 2015; for the updated configuration information B2, the device manager 140-1 indicates the publication date of Apr. 6, 2015; for the updated configuration information F4, the device manager 140-1 indicates the publication date of Apr. 6, 2015; etc.

In addition to updating the configuration information 120-1 stored in the medical device 110-1, subsequent to updating the respective configuration information 120-1 in a manner as previously discussed, the device manager 140-1 updates the synchronization date associated with the medical device 110-1 to the current day of Apr. 7, 2015 when the medical device 110-1 is synchronized.

In this manner, as new updates are published and subsequently stored in the repository 180, the configuration manager resource 150 initiates distribution of incremental updates of configuration information as opposed to transmitting all of the configuration information 183 to the medical device 110-1.

Accordingly, assuming that the configuration updates to configuration information 183 occur at a relatively low rate, the amount of traffic over network 190-2 is substantially reduced. Additionally, the configuration information 120-1 can be updated much more quickly based upon updating incremental sets of configuration information on an as-needed basis (such as when a respective newer configuration information is available), making it possible to more quickly update configuration information 120-1 in the medical device 110-1. As an illustrative example, it may require several minutes to download the complete copy of the configuration information 183 to the medical device 110-1. In contrast, as described herein, downloading incremental configuration update information to the medical device 110-1 may occur in several seconds or less.

Additionally, if desired, subsequent to updating the corresponding configuration information 120-1 in the medical device 110-1 based upon the incremental configuration update information received from the configuration manager resource 150, the device manager 140-1 can be configured to display a respective notification on display screen 130 to notify the corresponding user 118-1 that the configuration information 120-1 in the medical device 110-1 has been updated and synchronized with the configuration information 183 in the repository 180.

Figure 5:
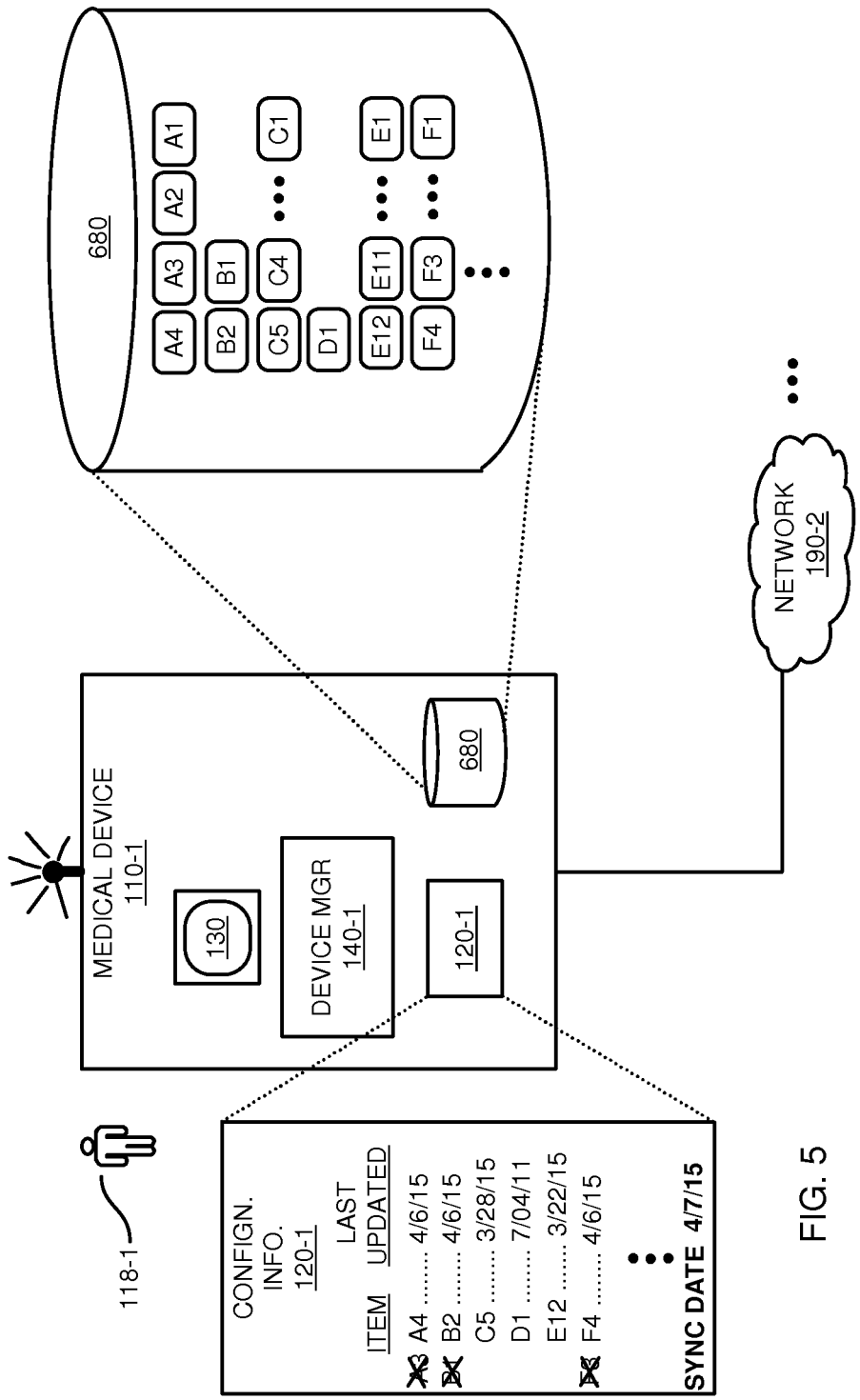
FIG. 5 is an example diagram illustrating storage and management of multiple prior versions of configuration information according to embodiments herein.

FIG. 5 is an example diagram illustrating storage of prior versions of configuration information for each of multiple different items according to embodiments herein.

In certain embodiments, it may be useful to store previous versions of configuration information in the medical device 110-1. In such an instance, the device manager 140-1 stores the previous versions of configuration information in the corresponding local repository 680 as opposed to deleting old versions of configuration information after a respective update is received for a given item.

If desired, prior versions of configuration information stored in repository 680 can be deleted when it is known that they are no longer going to be used or needed by the medical device 110-1.

In one embodiment, as an alternative to storing the older versions of configuration information locally in the medical device 110-1, the configuration management resource 150 can be configured to store the older, previously published, versions of configuration information in remote repository 180. In such an instance, if an older version of configuration information (not stored in the medical device 110-1) is required by a respective medical device 110-1 or corresponding user, the medical device 110-1 can be configured to communicate with the configuration management resource 150 to obtain the prior version of configuration information.

Figure 6:
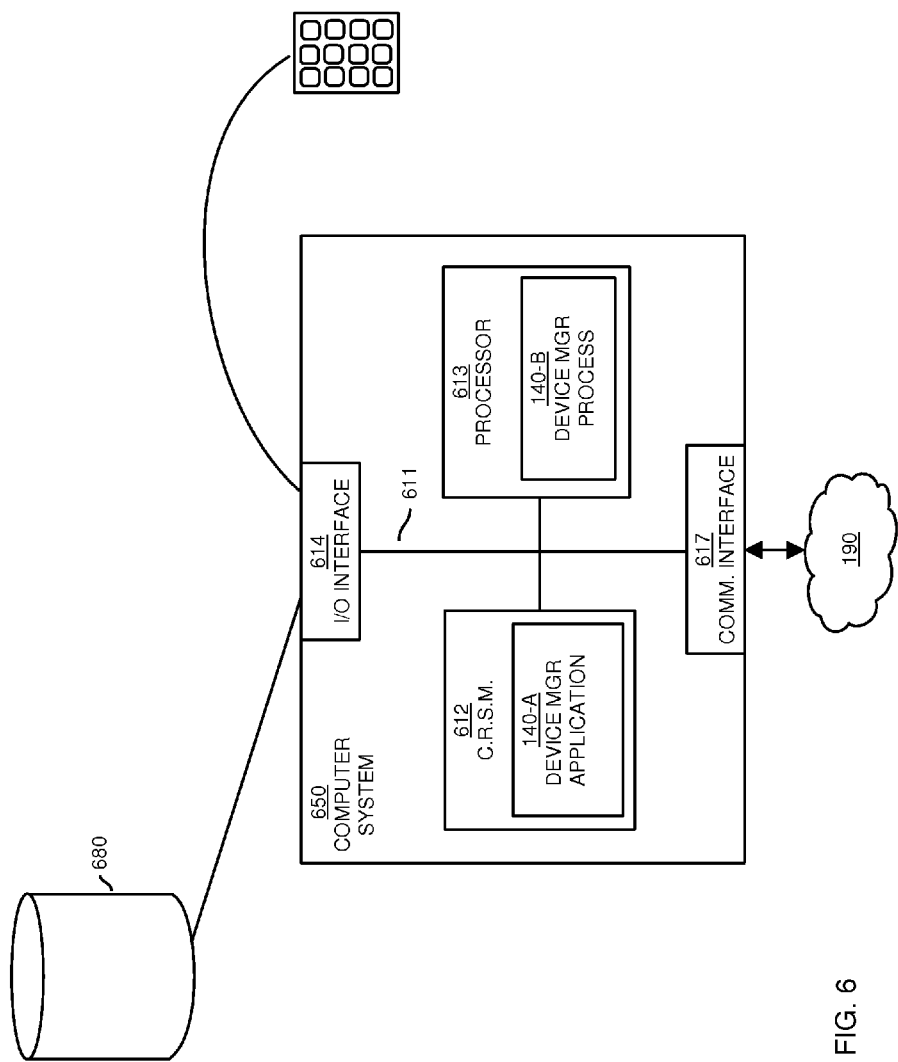
FIG. 6 is a diagram illustrating an example computer architecture in which to execute any of the functionality according to embodiments herein.

FIG. 6 is an example block diagram of a computer device for implementing any of the operations as discussed herein.

As shown, computer system 650 such as a computer device of the present example can be disposed in any of medical devices 110, editor resource 111, the configuration management resource 150, publisher resource 115, etc., to execute operations as discussed herein.

In this example embodiment, computer system 650 includes an interconnect 611 that couples computer readable storage media 612 such as a non-transitory type of media (i.e., any type of hardware storage medium, tangible storage medium, etc.) in which digital information can be stored and retrieved, a processor 613 (e.g., one or more processor devices, computer processor hardware, or hardware processors), I/O interface 614, and a communications interface 617. Communications interface 617 enables the computer system 650 to communicate with other network elements present in a corresponding network environment.

I/O interface 614 provides connectivity to a repository 680 and, if present, other devices such as a playback device, display screen, keypad, a computer mouse, etc.

Computer readable storage medium 612 can be any hardware storage resource or device such as memory, optical storage, hard drive, floppy disk, etc. In one embodiment, the computer readable storage medium 612 stores instructions and/or data.

Communications interface 617 enables the computer system 650 and corresponding processor 613 to communicate with network elements in communication environment 100 retrieve information from remote sources such as network elements and communicate with other computers. I/O interface 614 enables processor 613 to retrieve stored information from repository 680.

As shown, computer readable storage media 612 is encoded with device manager application 140-A (e.g., software, firmware, computer code, etc., associated with device manager 140) or other suitable application executed by processor 613. Device manager application 140-A can be configured to include instructions to implement any of the operations as discussed herein.

During operation of one embodiment, processor 613 accesses computer readable storage media 612 via the use of interconnect 611 in order to launch, run, execute, interpret or otherwise perform the instructions in device manager application 140-A stored on computer readable storage medium 612.

Execution of the device manager application 140-A produces processing functionality such as device manager process 140-B in processor 613. In other words, the device manager process 140-B associated with processor 613 represents one or more aspects of executing device manager application 140-A within or upon the processor 613 in the computer system 650.

Those skilled in the art will understand that the computer system 650 can include other processes and/or software and hardware components, such as an operating system that controls allocation and use of hardware resources to execute device manager application 140-A.

In accordance with different embodiments, note that computer system 650 may be any of various types of devices, including, but not limited to, a mobile computer, a medical device, infusion pump, a personal computer system, a server resource, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. The computer system 650 may reside at any location or can be included in any suitable resource in communication environment 100 to implement functionality as discussed herein.

Functionality supported by the different resources will now be discussed via flowcharts in FIGS. 7-8. Note that the steps in the flowcharts below can be executed in any suitable order.

Figure 7:
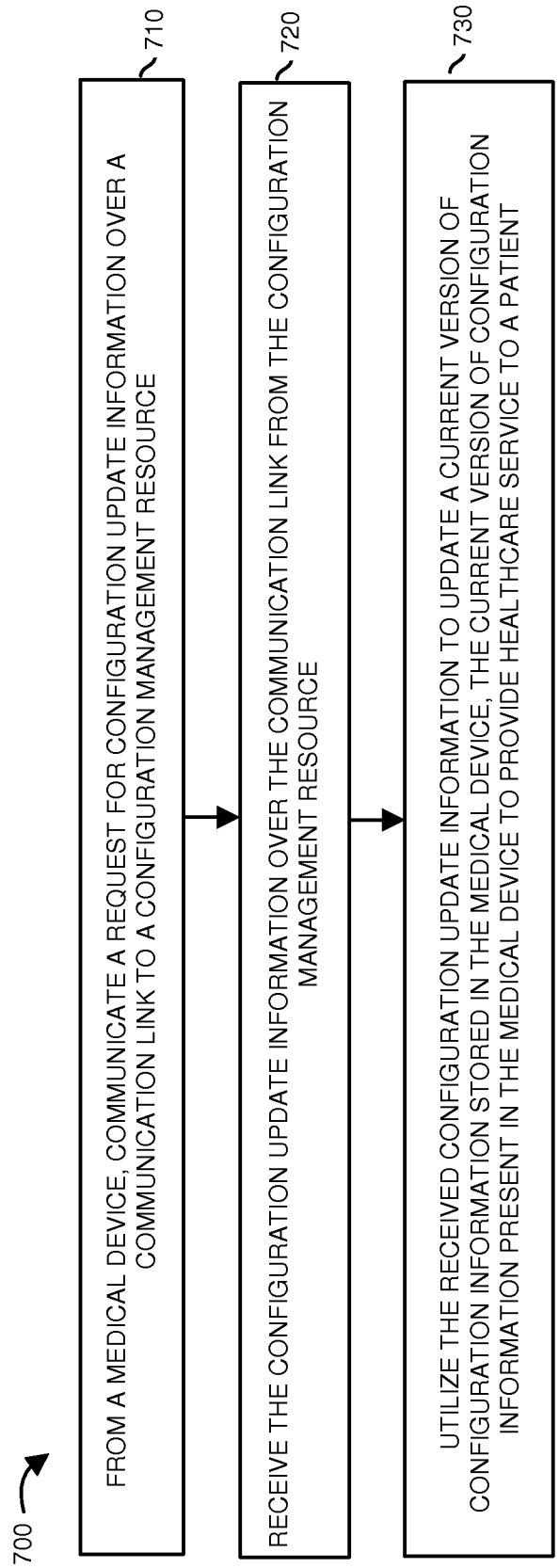
FIG. 7 is an example diagram illustrating a method according to embodiments herein.

FIG. 7 is a flowchart 700 illustrating an example method according to embodiments. Note that there will be some overlap with respect to concepts as discussed above.

In processing block 710, via published updates 212, the configuration management resource 150 receives an update (such as configuration update B2) for application to a particular set of configuration information B1 stored in repository 180.

In processing block 720, the configuration management resource 150 applies the received configuration update B2 to the particular set of configuration information B1.

In processing block 730, the configuration management resource 150 manages access to the configuration information 183 stored in the repository 180. As previously discussed, the configuration information 183 includes multiple sets of configuration information (such as configuration information A4, configuration information B2, configuration information C5, etc.) for distribution to medical devices 110 in network environment 100.

In a similar manner, as content update information is published, the configuration management resource 150 incrementally updates each of the sets of configuration information stored in repository 180.

Figure 8:
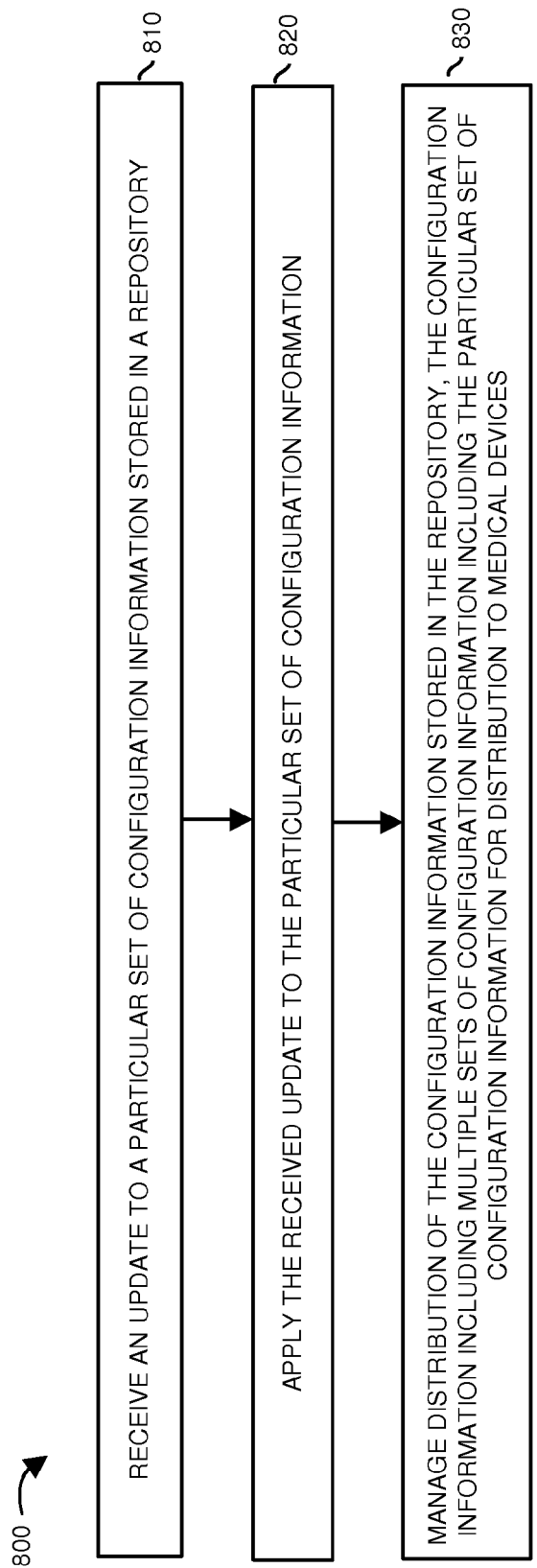
FIG. 8 is an example diagram illustrating a method according to embodiments herein.

FIG. 8 is a flowchart 800 illustrating an example method according to embodiments herein. Note that there will be some overlap with respect to concepts as discussed above.

In processing block 810, the medical device 110-1 communicates a request 420 for configuration update information over a communication link 327-1 to configuration management resource 150.

In processing block 820, the medical device 110-1 receives the configuration update information (such as configuration information A4) over the communication link 327-1 from the configuration management resource 150.

In processing block 830, the device manager 140-1 of the medical device 110-1 utilizes the received configuration update information A4 to update a current version of configuration information A3 stored in the medical device 110-1. As previously discussed, the current version of configuration information such as configuration information A3 present in the medical device A3 was previously used to provide healthcare service to a patient. Because the configuration information A3 has been updated, the configuration information A4 is now available for use by the medical device 110-1 to administer a respective drug to a target recipient.

In a similar manner, as updates are available, the device manager 140-1 incrementally updates each of the sets of configuration information stored in the medical device 110-1.

Figure 9:
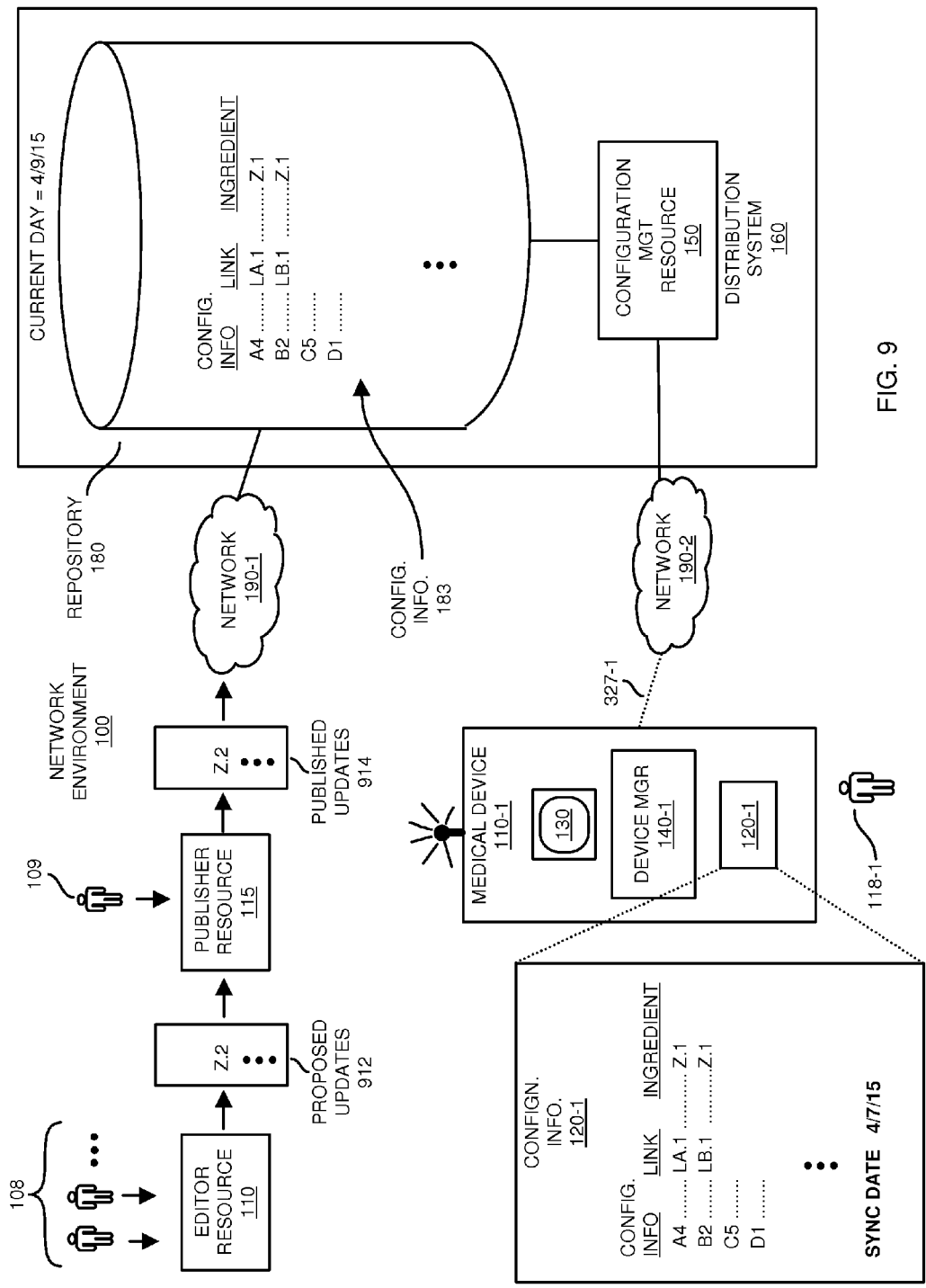
FIG. 9 is an example diagram illustrating another technique of updating configuration information according to embodiments herein.

FIG. 9 is an example diagram illustrating application of further possible updates to configuration information according to embodiments herein.

Note that each of the drugs A, B, C, etc., can include any number of links (such as zero or more links) specifying information about corresponding active pharmaceutical ingredients in each drug. In this example embodiment, assume that each of drug A and drug B include active pharmaceutical ingredient Z. Accordingly, drug A and drug B are related because they include the same ingredient.

As shown, the configuration information 183 stored in a repository 180 includes a corresponding link LA.1 to corresponding ingredient information Z.1. The link LA.1 indicates that drug A includes ingredient Z as specified by ingredient information Z.1.

As further shown, the configuration information stored in repository 180 includes corresponding link LB.1 to corresponding ingredient information Z.1 as well. The link LB.1 indicates that drug B includes ingredient Z as specified by ingredient information Z.1

Further in this example embodiment, based upon input from administrator 109, assume that the publisher resource 115 publishes an update to ingredient information Z1. For example, ingredient information Z.1 is updated to ingredient information Z.2 as indicated by published updates 914.

Prior to updating any drugs and corresponding information in the repository 180 that include ingredient Z based on published updates 914 including Z.2, as shown, the data stored in repository includes configuration information 183 as previously discussed. In this example embodiment, via link LA.1, the repository 180 stores information indicating that drug A includes ingredient Z as specified by corresponding ingredient information Z.1. In other words, the link LA 0.1 associated with configuration information A4 indicates that drug A includes ingredient information Z.1. Additionally, via link LB.1, the repository 180 indicates that drug B includes ingredient Z as specified by ingredient information Z.1.

In a similar manner as previously discussed, prior to updating using published updates 914, assume that the configuration management resource 150 initiated distribution of the data stored in repository 180 to medical device 110-1 as configuration information 120-1. As shown, the configuration information 120-1 stored in medical device 110-1 includes link LA.1 and link LB.1 to indicate that both drugs A and B include ingredient Z as specified by ingredient information Z.1. The following figure illustrates updating of configuration information 183 in repository 180 and distribution to medical device 110-1.

Figure 10:
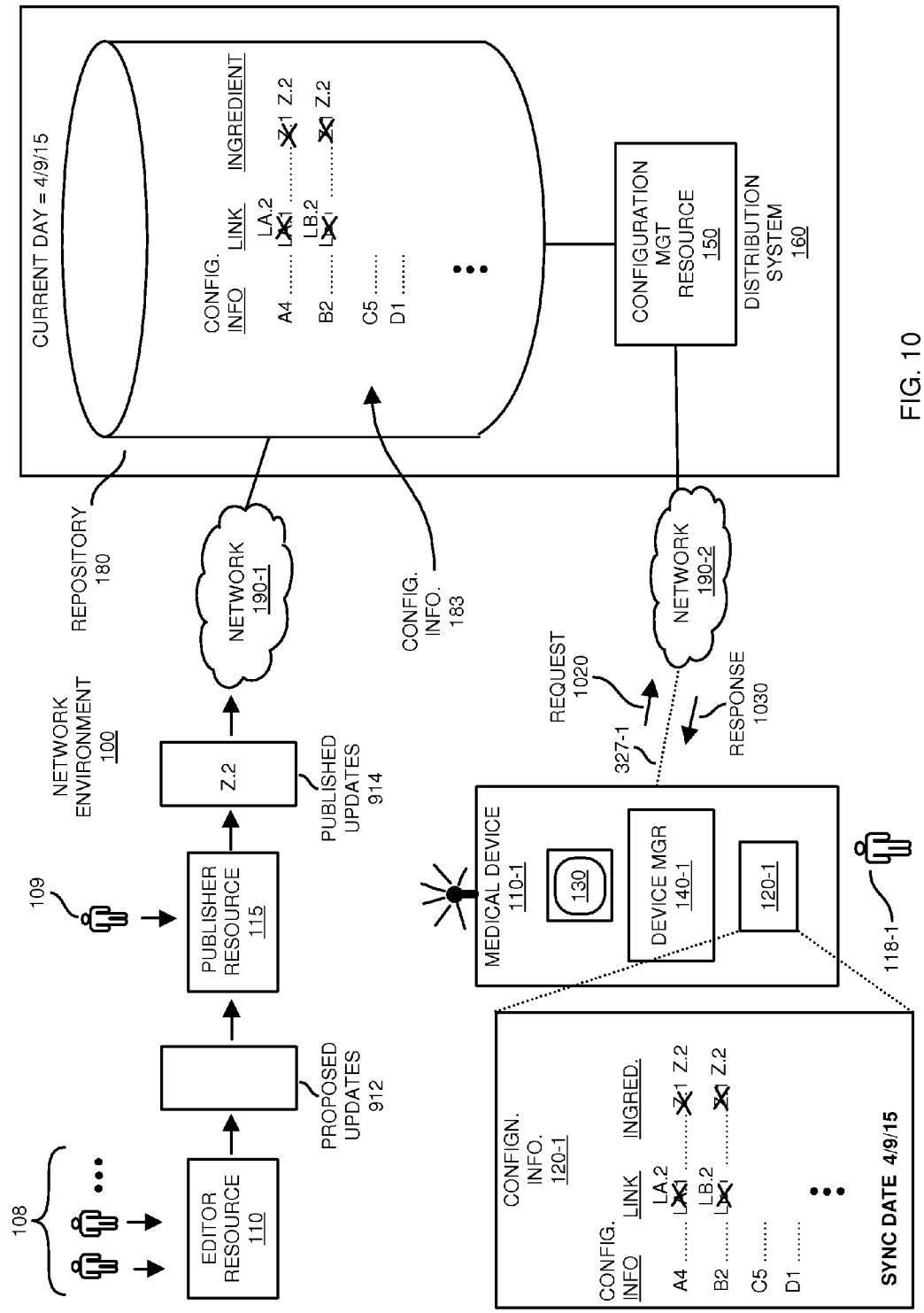
FIG. 10 is an example diagram illustrating updating configuration information and distribution of updated configuration information according to embodiments herein.

FIG. 10 is an example diagram illustrating updates to link information according to embodiments herein.

As shown, the configuration management resource 150 receives published updates 914 indicating that the ingredient information Z.1 is to be replaced with new ingredient information Z.2. To update corresponding configuration information 183 in repository 180, the configuration management resource 150 retrieves the updated ingredient information Z.2 and stores it in repository 180. For each of the drugs in repository that includes ingredient Z, the configuration manager resource 150 updates corresponding ingredient information Z.1 to Z.2. More specifically, in accordance with the published updates 914, the configuration management resource 150 replaces link LA.1 with link LA.2 to indicate the association of configuration information A4 to new ingredient information Z.2 instead of old information Z.1. Additionally, in accordance with the published updates 914, the configuration manager resource 150 replaces link LB.1 with link LB.2 to indicate the association of configuration information B2 to new ingredient information Z.2 instead of information Z.1.

In a similar manner as previously discussed, upon detecting that the configuration information 120-1 stored in medical device 110-1 is out of date with respect to the configuration information 183 stored in repository 180, the configuration management resource 150 initiates distribution of the updated link information and ingredient information to each of the medical devices 110. For example, in one embodiment, the medical device 110-1 generates and transmits the requested 1020 to configuration management resource 150 for updated configuration information. In response to receiving the request 1020, the configuration management resource 150 transmits response 1030 including the updated link information and corresponding ingredient information to the medical device 110-1 that, in turn, uses such information to update configuration information 120-1 as shown. In other words, the device manager 140-1 updates the configuration information 120-1 as shown to reflect the new information Z2.

Note again that techniques herein are well suited for managing modification and distribution of configuration information for use by medical devices. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A method comprising:
via a medical infusion pump:
communicating a request for configuration update information over a communication link to a configuration management resource;
receiving the configuration update information over the communication link from the configuration management resource, the received configuration update information indicating a modification to be applied to fluid delivery information for a first drug of multiple drugs in a drug library used by the medical infusion pump;
utilizing the received configuration update information to update a current version of configuration information stored in a repository of the medical infusion pump for the first drug, the current version of configuration information stored in the repository of the medical infusion pump to provide fluid delivery healthcare service to a patient;
utilizing the current version of configuration information to configure the medical infusion pump to administer the first drug to the patient; and
tracking individual versions of fluid delivery configuration information assigned to the multiple drugs updated in the drug library, the drug library incrementally updated with the individual versions of fluid delivery configuration information at different times.

2. The method as in claim 1, wherein the current version of configuration information is a set amongst multiple sets of independent configuration information stored in the medical infusion pump, each of the sets of independent configuration information specifying how to administer a corresponding treatment to the patient using the medical infusion pump.

3. The method as in claim 2, wherein the first drug is a first drug fluid;
wherein the multiple sets of independent configuration information includes: i) first configuration information specifying how to administer the first drug fluid using the medical infusion pump, ii) second configuration information specifying how to administer a second drug fluid using the medical infusion pump, and iii) third configuration information specifying how to administer a third drug fluid using the medical infusion pump;
wherein the configuration update information pertains to the first configuration information; and
wherein utilizing the configuration update information to update the current version of configuration information stored in the medical infusion pump further comprises: mapping the received configuration update information to the second configuration information and applying the configuration update information to the second configuration information.

4. The method as in claim 3, wherein utilizing the received configuration update information to update the current version of configuration information further comprises:
utilizing the received configuration update information to modify a set of fluid pump control information for the first drug, the set of fluid pump control information indicating how to control delivery of the first drug to a recipient using the medical infusion pump;
utilizing a first time stamp to track a time of modifying the first set of fluid pump control information for the first drug; and
maintaining a second time stamp to indicate a time of modifying a second set of fluid pump patrol information indicating how to control delivery of the second drug to a recipient using the medical infusion pump, the second time stamp specifying an earlier date than the first time stamp.

5. The method as in claim 1 further comprising:
mapping the configuration update information to the current version of configuration information; and
wherein utilizing the received configuration update information to update the current version of configuration information stored in the medical infusion pump further comprises: applying the configuration update information to the current version of the configuration information.

6. The method as in claim 1, wherein the request triggers retrieval of the configuration update information for the first drug.

7. The method as in claim 6, wherein the medical infusion pump generates the request in response to detecting an event in which the medical infusion pump is operated to deliver the first drug to the patient.

8. The method as in claim 1, wherein the drug library stores fluid pump delivery information for each of the multiple drugs, fluid update information for each of the multiple drugs retrieved individually by the medical infusion pump to update the drug library.

9. The method as in claim 1 further comprising:
using first time stamp information to track a time of updating the first drug with the received configuration update information; and
using second time stamp information to track a time of updating fluid delivery information for a second drug in the drug library, the second time stamp information indicating an earlier date than the first time stamp.

10. The method as in claim 9 further comprising:
tracking a time of updating each of the multiple drugs in the drug library.

11. The method as in claim 1 further comprising:
communicating the request in response to detecting that a less-than-all portion of the drugs in the drug library have available updates to respective fluid pump delivery information to control delivery of fluid form the medical infusion pump;
receiving updated fluid pump delivery information for each of the less-than-all portion of drugs; and
individually applying the updated fluid pump delivery information to the less-than-all portion of drugs in the drug library.

12. The method as in claim 11, wherein the request specifies to retrieve the configuration update information for the first drug.

13. The method as in claim 1, wherein utilizing the received configuration update information to update the current version of configuration information further comprises:
utilizing the received configuration update information to modify a set of fluid pump control information for the first drug, the set of fluid pump control information indicating how to control delivery of the first drug to a recipient using the medical infusion pump;

utilizing a first time stamp information to track a time of modifying the first set of fluid pump control information for the first drug; and maintaining a second time stamp to indicate a time of modifying a second set of fluid pump control information in the drug library, the second set of fluid pump control information indicating how to control delivery of a second drug to a recipient using the medical infusion pump, the second time stamp specifying an earlier date than the first time stamp.

14. The method as in claim 1 further comprising:

using first time stamp information to track a time of updating the first drug with the received configuration update information; and using second time stamp information to track a time of updating fluid delivery information for a second drug in the library, the second time stamp information indicating an earlier date than the first time stamp.

15. The method as in claim 1, wherein the drug library includes identities of the first drug and a second drug, the method further comprising:

at the medical infusion pump:

incrementally updating only the first drug in the drug library with the received configuration update information based on a first time of communicating with the configuration management resource; and incrementally updating only the second drug in the drug library based on a second instant in time of communicating with configuration management resource, the second time occurring after the first instant in time.

16. The method as in claim 1, wherein the drug library stores fluid pump delivery setting information for each of the multiple drugs, pump setting update information for each of the multiple drugs retrieved individually by the medical infusion pump to update the drug library.

17. The method as in claim 1 further comprising:

at the medical infusion pump: tracking individual times of updating the fluid delivery configuration information associated with the multiple drugs in the drug library.

18. The method as in claim 1, wherein the drug library of the medical infusion pump is incrementally updated with the individual versions of fluid delivery configuration information at different times as the individual versions of the fluid delivery configuration information become available as indicated by the communication management resource.

19. A method comprising:

from a medical infusion pump:

communicating a request for configuration update information over a communication link to a configuration management resource;

receiving the configuration update information over the communication link from the configuration management resource, the received configuration update information indicating a modification to be applied to fluid delivery information for a first drug of multiple drugs in a drug library used by the medical infusion pump;

utilizing the received configuration update information to update a current version of configuration information stored in a repository of the medical infusion pump for the first drug, the current version of configuration information stored in the repository of the medical infusion pump to provide fluid delivery healthcare service to a patient;

utilizing the current version of configuration information to configure the medical infusion pump to administer the first drug to the patient;

wherein communicating the request for configuration update information further comprises: from the medical infusion pump, communicating a publication time value of the current version of configuration information stored in the medical infusion pump to the configuration management resource; and wherein receiving the configuration update information over the communication link from the configuration management resource further comprises: receiving incremental updates that were published after the time value; and applying the incremental updates to specified portions of the current version of configuration information.

20. The method as in claim 19, wherein utilizing the configuration update information to update the current configuration information stored in the medical infusion pump further comprises:

replacing a specified portion of the current version of configuration information with the configuration update information.

21. The method as in claim 19, wherein utilizing the configuration update information to update the current configuration information stored in the medical infusion pump further comprises:

modifying a specified portion of the current version of configuration information in a manner as specified by the configuration update information.

22. The method as in claim 1 further comprising:

in response to a trigger event, establishing the communication link between the medical infusion pump and the configuration management resource, the configuration management resource selecting the configuration update information for distribution to the medical infusion pump based on a comparison of a publication time of last configuration update resident on the medical infusion pump and a time value indicating when the configuration update information was published for distribution.

23. A method comprising:

via computer processor hardware, executing operations of:

storing multiple sets of configuration information in a repository, the multiple sets of configuration information including a first set of configuration information for distribution to medical infusion pump devices;

receiving an update applicable to the first set of configuration information stored in the repository, the first set of configuration information pertaining to delivery of a first type of fluid;

applying the received update to the first set of configuration information to produce an updated first set of configuration information; and managing individual distribution of the updated first set of configuration information stored in the repository to the medical infusion pump devices.

24. The method as in claim 23 further comprising:

receiving first timestamp information, the first timestamp information specifying a time associated with application of the update to the first set of configuration information; and storing the first timestamp information associated with the first set of configuration information to indicate when the first set of configuration information was published for distribution to control the medical infusion pump devices.

25. The method as in claim 24 further comprising:
receiving second time stamp information, the second time stamp information specifying a time associated with application of an update to a second set of configuration information; and
storing the second time stamp information associated with the second set of configuration information to indicate when the second set of configuration information was published for distribution to control the medical infusion pump devices, the first timestamp information indicating a first date, the second timestamp information indicating a second date different than the first date.

26. The method as in claim 25 further comprising:
distributing the first timestamp information and the second timestamp information to the medical infusion pump devices to indicate respective dates in which the first set of configuration information and the second set of configuration information were updated.

27. The method as in claim 23, wherein receiving the update further comprises:
receiving notification from a publication management resource that the update is available for retrieval and distribution to the medical infusion pump devices.

28. The method as in claim 23, wherein managing individual distribution of the updated first set of configuration information stored in the repository further comprises:
receiving a request from a medical infusion pump device for retrieval of the updated first set of configuration information stored in the repository;
retrieving the updated first set of configuration information; and
forwarding the updated first set of configuration information to the medical infusion pump device.

29. The method as in claim 28, wherein the medical infusion pump utilizes the received update to update a specific drug in a drug library stored in the medical infusion pump device.

30. The method as in claim 23, wherein the multiple sets of configuration information stored in the repository is a drug library, each of the respective sets of configuration information including information facilitating treatment of a respective patient using a drug to which the respective set of configuration information pertains.

31. The method as in claim 23 further comprising:
receiving a time value specifying when configuration information stored in a medical infusion pump device was published;
identifying which of the multiple sets of configuration information in the repository were updated subsequent to the time specified by the time value; and
forwarding the identified set of configuration information to the medical infusion pump device.

32. The method as in claim 23, wherein the multiple sets of configuration information represents a drug library; and
wherein managing individual distribution of the updated first set of configuration information to the first medical infusion pumps includes: in response to receiving a request for the updated first set of configuration information from a first medical infusion pump, communicating the updated first set of configuration information to the first medical infusion pump.

33. The method as in claim 32, wherein the first medical infusion pump is operable to: i) store the first set of configuration information, and ii) replace the first set of configuration information with the updated configuration information.

34. The method as in claim 33, wherein the first medical infusion pump is operable to generate the request in response to detecting that the first set of updated configuration information is available as a replacement to the first set of configuration information stored in the first medical infusion pump.

35. A computer system comprising:
computer processor hardware; and
a hardware storage resource coupled to the computer processor hardware, the hardware storage resource storing instructions that, when executed by the computer processor hardware, causes the computer processor hardware to perform operations of:
communicating a request for configuration update information over a communication link to a configuration management resource;
receiving the configuration update information over the communication link from the configuration management resource; and
utilizing the received configuration update information to update a current version of configuration information stored in a medical infusion pump device, the current version of configuration information present in the medical infusion pump device to provide healthcare service to a patient;
wherein communicating the request for configuration update information further comprises: from the medical infusion pump device, communicating a publication time value of the current version of configuration information stored in the medical infusion pump device to the configuration management resource;
wherein receiving the configuration update information over the communication link from the configuration management resource further comprises: receiving incremental updates that were published after the publication time value; and
applying the incremental updates to specified portions of the current version of configuration information.

36. The computer system as in claim 35, wherein the current version of configuration information is part of a drug library stored in the medical infusion pump device.

37. The computer system as in claim 36, wherein the drug library includes usage information with respect to multiple different drugs selectively administered to the patient using the medical infusion pump, the received configuration update information pertaining to one of multiple drugs in the drug library.

38. The computer system as in claim 35, wherein the current version of configuration information is a set amongst multiple sets of independent configuration information stored in the medical infusion pump device, each of the sets of independent configuration information specifying how to administer a corresponding treatment to the patient using the medical infusion pump device.

39. The computer system as in claim 38, wherein the multiple sets of independent configuration information includes: i) first configuration information specifying how to administer a first drug treatment using the medical infusion pump device, ii) second configuration information specifying how to administer a second drug treatment using the medical infusion pump device, and iii) third configuration information specifying how to administer a third drug treatment using the medical infusion pump device;

wherein the configuration update information pertains to the second configuration information; and wherein utilizing the configuration update information to update the current version of configuration information stored in the medical infusion pump device further comprises: mapping the received configuration update information to the second configuration information and applying the configuration update information to the second configuration information.

40. The computer system as in claim 35, wherein the computer processor hardware further performs operations of:

mapping the configuration update information to the current version of configuration information; and wherein utilizing the received configuration update information to update the current version of configuration information stored in the medical infusion pump device further comprises: applying the configuration update information to the current version of the configuration information.

41. Computer-readable hardware storage having instructions stored thereon, the instructions, when carried out by computer processor hardware, cause the computer processor hardware to:

communicate a request for configuration update information over a communication link to a configuration management resource;

receive the configuration update information over the communication link from the configuration management resource, the received configuration update information indicating a modification to be applied to fluid delivery information for a first drug of multiple drugs in a drug library used by the medical infusion pump;

utilize the received configuration update information to update a current version of configuration information stored in a repository of the medical infusion pump for the first drug, the current version of configuration information stored in the repository of the medical infusion pump to provide fluid delivery healthcare service to a patient;

utilize the current version of configuration information to configure the medical infusion pump to administer the first drug to the patient; and track individual versions of fluid delivery configuration information assigned to the multiple drugs updated in the drug library, the drug library incrementally updated with each of the individual versions of fluid delivery configuration information at different times.

42. A method comprising:

via a medical infusion pump:

communicating a request for configuration update information over a communication link to a configuration management resource;

receiving the configuration update information over the communication link from the configuration management resource, the received configuration update information indicating a modification to be applied to fluid delivery information for a first drug of multiple drugs in a drug library used by the medical infusion pump;

utilizing the received configuration update information to update a current version of configuration information stored in a repository of the medical infusion pump for the first drug, the current version of configuration information stored in the repository of the medical infusion pump to provide fluid delivery healthcare service to a patient;

utilizing the current version of configuration information to configure the medical infusion pump to administer the first drug to the patient; and wherein the request triggers retrieval of the configuration update information for the first drug in response to detecting availability of the configuration update information for the first drug.

* * * * *

UNITED STATES PATENT AND TRADEMARK OFFICE
CERTIFICATE OF CORRECTION

PATENT NO. : 10,025,909 B2
APPLICATION NO. : 14/794231
DATED : July 17, 2018
INVENTOR(S) : George W. Gray and William C. McQuaid It is certified that error appears in the above-identified patent and that said Letters Patent is hereby corrected as shown below:

In the Claims

Column 17, Line 1 delete "information".

Signed and Sealed this
Twenty-fifth Day of February, 2020

Andrei Iancu
*Director of the United States Patent and Trademark Office*